US012558281B2

(12) United States Patent
Wang et al.

(10) Patent No.: US 12,558,281 B2
(45) Date of Patent: Feb. 24, 2026

(54) ROTATING CUSHIONING AND ASSISTING MECHANISM AND AN EXOSKELETON ANKLE JOINT CUSHIONING AND ASSISTING DEVICE

(71) Applicant: SHANGHAI FOURIER INTELLIGENCE CO., LTD, Shanghai (CN)

(72) Inventors: Jun Wang, Jiangsu (CN); Danping Xiao, Jiangxi (CN); Jie Gu, Shanghai (CN); Chong Li, Shanghai (CN)

(73) Assignee: SHANGHAI FOURIER INTELLIGENCE CO., LTD, Shanghai (CN)

( * ) Notice: Subject to any disclaimer, the term of this patent is extended or adjusted under 35 U.S.C. 154(b) by 553 days.

(21) Appl. No.: 18/027,923

(22) PCT Filed: Aug. 5, 2021

(86) PCT No.: PCT/CN2021/110784
§ 371 (c)(1),
(2) Date: Mar. 22, 2023

(87) PCT Pub. No.: WO2022/062706
PCT Pub. Date: Mar. 31, 2022

(65) Prior Publication Data
US 2023/0372180 A1     Nov. 23, 2023

(30) Foreign Application Priority Data

Sep. 28, 2020     (CN) .......................... 202011037284.3

(51) Int. Cl.
*A61H 1/02*          (2006.01)
*A61F 5/01*          (2006.01)

(52) U.S. Cl.
CPC ......... *A61H 1/0214* (2013.01); *A61H 1/0266* (2013.01); *A61F 2005/0155* (2013.01); *A61H 2001/0207* (2013.01)

(58) Field of Classification Search
CPC .......... A61H 1/0214; A61H 1/02; A61H 1/00; A61H 1/0274; A61H 1/0266;
(Continued)

(56) References Cited

U.S. PATENT DOCUMENTS 2,295,758 A  *  9/1942  Safford ................... F16D 65/46
                                                          188/196 R
4,872,665 A  * 10/1989  Chareire ............... A61F 5/0102
                                                          601/35

(Continued)

FOREIGN PATENT DOCUMENTS

CN          101021239 B      5/2010
CN          101829005 A      9/2010
(Continued)

OTHER PUBLICATIONS

Extended European Search Report issued in corresponding EP application No. 21871083.8 dated Jan. 2, 2024.
(Continued)

*Primary Examiner* — Timothy A Stanis
*Assistant Examiner* — Tyler A Raubenstraw
(74) *Attorney, Agent, or Firm* — HAUPTMAN HAM, LLP

(57)          ABSTRACT

A rotating cushioning and assisting mechanism comprises a rotating outward expanding member, an elastic return member, and an inner support heterogeneous member; the rotating outward expanding member comprises a first rotating member and a second rotating member, which enclose to form an expandable compartment; the elastic return member is connected to the free ends of the first rotating member and
(Continued)

the second rotating member; and the inner support heterogeneous member is rotationally disposed in the expandable compartment. When an external force drives the inner support heterogeneous member to rotate in the expandable compartment, a work done by the force exerted by the inner support heterogeneous member is converted into elastic potential energy to be stored; when the external force is over, the elastic potential energy is released and converted into kinetic energy to help the free ends of the two rotating members to move close.

19 Claims, 5 Drawing Sheets

(58) Field of Classification Search
CPC ............... A61H 1/0218; A61H 1/0281; A61H 2201/0207; A61H 2201/0165; A61H 2201/164; A61H 2201/165; A61H 2201/1671; A61H 2201/1676; A61H 2201/1454; A61H 2201/1614; A61H 2201/1642; A61H 3/00; A61F 5/013; A61F 5/0127; A61F 5/0102; A61F 5/01; A61F 2005/0155; A61F 2005/0169; A61F 2005/0179; F16F 15/067; B25J 9/0006
See application file for complete search history.

(56) References Cited

U.S. PATENT DOCUMENTS

| | | | | |
|---|---|---|---|---|
| 5,031,606 | A * | 7/1991 | Ring, Sr. ............... | A61F 5/0125 602/30 |
| 5,242,379 | A * | 9/1993 | Harris ................... | A61F 5/0111 602/65 |
| 5,267,924 | A | 12/1993 | Miller et al. | |
| 5,348,532 | A | 9/1994 | Prahl | |
| 5,520,627 | A | 5/1996 | Malewicz | |
| 5,954,677 | A * | 9/1999 | Albrecht ............... | A61F 5/0125 602/26 |
| 9,398,970 | B1 * | 7/2016 | Meyer ................... | A61F 5/0111 |
| 9,445,931 | B2 * | 9/2016 | Imaida ................... | A61F 5/01 |
| 10,314,680 | B2 * | 6/2019 | Pflaster ............... | A61B 5/1071 |
| 10,709,583 | B2 * | 7/2020 | Lefeber ................ | A61F 2/6607 |
| 10,751,884 | B2 * | 8/2020 | Woo ..................... | B25J 17/0208 |
| 10,799,381 | B2 * | 10/2020 | Lee ...................... | A61F 5/0102 |
| 11,400,010 | B2 * | 8/2022 | Smith .................. | A61H 1/0266 |
| 11,491,074 | B2 * | 11/2022 | Witte .................. | A61H 1/0237 |
| 2003/0093018 | A1 | 5/2003 | Albrecht et al. | |
| 2012/0289870 | A1 * | 11/2012 | Hsiao-Wecksler ....... | A61H 3/00 601/5 |
| 2014/0308065 | A1 * | 10/2014 | DeHarde ................. | F16F 1/10 403/113 |
| 2015/0313786 | A1 * | 11/2015 | Sano ....................... | A61H 3/00 602/16 |
| 2016/0136033 | A1 * | 5/2016 | Johnston ............ | A61H 15/0092 601/129 |
| 2017/0246740 | A1 * | 8/2017 | Barnes ................. | B25J 19/0016 |
| 2017/0281390 | A1 * | 10/2017 | Abdul-Hafiz ......... | A61F 5/0125 |
| 2017/0303643 | A1 * | 10/2017 | Converse ............... | A43C 11/00 |
| 2018/0161188 | A1 * | 6/2018 | Zistatsis ................. | A61H 1/024 |
| 2018/0289512 | A1 * | 10/2018 | Fujikake .............. | A61F 2/6607 |
| 2019/0175364 | A1 | 6/2019 | Schimmels et al. | |
| 2019/0224031 | A1 | 7/2019 | Dunca | |
| 2019/0262214 | A1 * | 8/2019 | Smith .................... | A61H 1/024 |
| 2019/0374364 | A1 * | 12/2019 | Wu .................... | A63B 21/4011 |
| 2020/0022821 | A1 * | 1/2020 | Mooney ................. | B25J 9/0006 |
| 2020/0139537 | A1 * | 5/2020 | Moisè ...................... | A61H 3/00 |
| 2020/0170809 | A1 * | 6/2020 | Etenzi ...................... | A61F 2/74 |
| 2020/0197209 | A1 * | 6/2020 | Bejarano .............. | A61F 5/0125 |
| 2021/0053208 | A1 * | 2/2021 | Paine .................... | B25J 9/0006 |
| 2021/0196483 | A1 * | 7/2021 | Boiten ...................... | A61F 2/64 |

FOREIGN PATENT DOCUMENTS

| | | |
|---|---|---|
| CN | 103210238 A | 7/2013 |
| CN | 104771292 A | 7/2015 |
| CN | 105616113 A | 6/2016 |
| CN | 106236502 A | 12/2016 |
| CN | 207462306 U | 6/2018 |
| CN | 108784902 A | 11/2018 |
| CN | 109262596 A | 1/2019 |
| CN | 109381841 A | 2/2019 |
| CN | 209662127 U | 11/2019 |
| CN | 111084681 A | 5/2020 |
| CN | 111249047 A | 6/2020 |
| CN | 210991569 U | 7/2020 |
| DE | 3610570 A1 | 10/1987 |
| DE | 4038511 A1 | 6/1992 |
| DE | 102018204597 A1 | 10/2019 |
| EP | 0027762 A1 | 4/1981 |
| EP | 1053767 B1 | 5/2005 |
| EP | 3388043 A1 | 10/2018 |
| WO | 9309734 A1 | 5/1993 |
| WO | 2016121019 A1 | 8/2016 |
| WO | 2017050824 A1 | 3/2017 |

OTHER PUBLICATIONS

Examination Report issued in corresponding EP application No. 21871083.8 dated Jan. 18, 2024.
WIPO, International Search Report for International Application No. PCT/CN2021/110784, Oct. 20, 2021.
First Office Action issued in corresponding CN application No. 202011037284.3 dated Nov. 19, 2020.

* cited by examiner

ROTATING CUSHIONING AND ASSISTING MECHANISM AND AN EXOSKELETON ANKLE JOINT CUSHIONING AND ASSISTING DEVICE

FIELD OF TECHNOLOGY

The present invention relates to the technical field of medical rehabilitation devices, in particular to a rotating cushioning and assisting mechanism and an exoskeleton ankle joint cushioning and assisting device.

BACKGROUND

With the continuous development of medical science and technology, rehabilitation therapy has become a new therapeutic discipline to promote the rehabilitation of physical and mental functions of patients and disabled people, and it is also a new technical specialty. Its purpose is to enable people to resume their daily life, study, work and labor, as well as social life as possible, integrate into society and improve their quality of life.

Patients with limb loss of mobility and muscle atrophy due to cerebrovascular disease, brain trauma and other causes often rely on passive exercise with the external force for rehabilitation training, so as to help them recover limb strength. When patients are trained passively by rehabilitation robots, it can not only effectively avoid the muscle atrophy caused by lack of exercise, but also effectively improve the rehabilitation effect of the wearer. In rehabilitation training, joint rehabilitation is an important rehabilitation object. Taking an ankle joint as an example, in the existing ankle joint devices:

①  Referring to a patent application with publication number CN105616113A, entitled "A Passive Energy Storage Foot Mechanism for Power Assisting Exoskeletons for Lower Limbs", filed by Southeast University. This type of exoskeleton ankle joint uses a dorsiflexion passive spring energy storage unit and a plantarflexion passive spring energy storage unit, which are connected to an ankle joint unit by a spring support unit and use a lateral plate of the foot as a fixed base, to complete dorsiflexion and plantarflexion passive energy storage respectively during exercise. It is possible to store and release energy when users walk to realize cushioning, shock absorption and automatic return. 1. After the product is finalized, when the dorsiflexion and plantarflexion are completed, the rotational torque at the ankle joint is set and cannot be adjusted. For different user groups, due to the difference of body types, such as fat, moderate and thin, the torque required at the ankle joint is slightly different, and the user experience is poor. 2. If the spring elasticity is selected small, the cushioning effect is not good; if the spring elasticity is selected large, the assembly experience is not very good when installing preload. 3. The design solution is slightly large in size, which has a slight influence on the appearance and modeling.

②  Referring to a patent with the patent grant announcement number CN104161610B, entitled "An Ankle Joint for External Skeleton Cushioning and Power Assisting", filed by Zhejiang University. The ankle joint for external skeleton cushioning and assisting comprises an ankle ball socket, an ankle ball head, a rubber washer and an ankle seat; a hole is provided in the middle of the ankle seat, the hole is connected with the shaft interference in an interference fit way, the ankle ball socket is hinged with the ankle ball head, a boss is welded on the ankle ball head, a groove is provided on the ankle ball socket, the boss on the ankle ball head can protrude from the groove; the rubber washer is arranged between the ankle seat and the ankle ball socket, and a contact surface of the rubber washer and the ankle ball socket is a plane; when the ankle joint flexes and extends, abducts and adducts, the rubber washer will be compressed to store energy and release energy when it recovers to its original shape, thus achieving the functions of cushioning and assisting. After the product is finalized, when the dorsiflexion and plantarflexion are completed, the rotational torque at the ankle joint is set and cannot be adjusted. For different user groups, due to the difference of body types, such as fat, moderate and thin, the torque required at the ankle joint is slightly different, and the user experience is poor. When a rubber washer is used for energy storage, the rubber will wear and age over time, which will affect the reliability and service life of products. Moreover, the energy storage effect of rubber used in this solution needs to be considered.

③  Referring to a patent with the publication announcement number CN111084681A, entitled "A Hydraulic Bionic Ankle Joint", filed by "BEIJING GOODOING SPEEDSMART TECH CO., LTD." The hydraulic bionic ankle joint comprises a permanent seat of which the lower end can be connected to a carbon fiber energy storage foot; a hydraulic buffer mechanism is pressed on the permanent seat, wherein a rotating shaft of the hydraulic buffer mechanism is parallel to a coronary shaft, to provide damping force during plantarflexion and dorsiflexion of the bionic ankle joint; and a square pyramid frustum structural member of which an upper end can be connected to an artificial limb receiving cavity and a lower end is connected to a rotating shaft of the hydraulic buffer mechanism, and the square pyramid frustum structural member can rotate and swing forwards and backwards around the rotating shaft of the hydraulic buffer mechanism. This solution requires a hydraulic device, which is costly and will bring about an increase in weight and size. For this reason, the present invention came into being.

SUMMARY

In view of the above situation, the primary purpose of the present invention is to provide a rotating cushioning and assisting mechanism and an exoskeleton joint mechanism with cushioning and return functions (i.e., resistance cushioning and assisted return), which can adjust the joint torque according to the needs of different body types. The mechanism comprises:

a rotating outward expanding member comprising a first rotating member and a second rotating member, which enclose to form an expandable compartment, one ends of the first rotating member and the second rotating member are pivot ends, and the other ends are free ends;

an elastic return member connected to the free ends of the first rotating member and the second rotating member; and an inner support heterogeneous member rotationally disposed in the expandable compartment, and an outward expanding force is applied on the first rotating member and the second rotating member on both sides of the expandable compartment along with the rotation of the inner support heterogeneous member, to stretch the elastic return member.

By adopting the technical solution, the present invention has the following technical effects:

The present invention connects the free ends of the first rotating member and the second rotating member through an elastic return member; when an external force drives the inner support heterogeneous member to rotate in the expandable compartment, an outward expanding force is exerted on the first rotating member and the second rotating member to make the two free ends move away from each other, so that the elastic return member is stretched as the free ends of the two rotating members move away from each other; at this time, a work done by the force exerted by the inner support heterogeneous member is converted into elastic potential energy to be stored, which plays a role in cushioning and damping the external force during the storage process; when the external force is over, the elastic potential energy is released and converted into kinetic energy to help the free ends of the two rotating members to move close, thus playing a role in assisted return.

Further, the rotating cushioning and assisting mechanism also includes a pitch-adjustable member, one end of the elastic return member is connected to the first rotating member through the pitch-adjustable member, and the other end is connected to the second rotating member; and the pitch-adjustable member comprises:

a chute provided at the free end of the first rotating member;

a limit permanent seat disposed in the chute and limited in the sliding direction of the chute, and provided with a perforation;

a pitch-adjusting slider disposed in the chute and provided with a threaded hole facing the perforation, and the elastic return member being connected to the pitch-adjusting slider; and a pitch-adjusting threaded member, one end of which threaded through the perforation and screwed into the threaded hole, and the other end having a stop portion which stops at the limit permanent seat.

The position of the pitch-adjusting slider in the chute is driven by a thread depth of the pitch-adjusting threaded member in the pitch-adjusting slider, which realizes the pre-stretching of the elastic return member, and thus playing a role of adjusting the torque to adapt to different users.

Further, the limit permanent seat can also be disposed on the free end of the first rotating member. As a component of fitting the pitch-adjusting threaded member, the core function of limit permanent seat is to keep the position unchanged, and it is a practical choice to set it on the chute or the free end of the first rotating member.

Further, the elastic return member is a spring or an elastic rubber resin. Alternatively, other members that can realize elastic stretching and return can be used.

Further, the rotating cushioning and assisting mechanism also includes a connecting rod comprising a rod body and a mounting housing, one end of the rod body is connected to the mounting housing and the other end is connected to an external structure; and the rotating outward expanding member is located in the mounting housing, and the expansion of the rotating outward expanding member is limited by the wall of the mounting housing. The main function of the mounting housing is to prevent the translocation of the rotating outward expanding member, and on the other hand, to set a restriction and limit for the expansion of the rotating outward expanding member.

The present invention also discloses an application of the rotating cushioning and assisting mechanism for cushioning and assisting in the exoskeleton joint rehabilitation exercise. Specifically, as long as the multi-degree of freedom movement of joints is involved, the principle of damping force cushioning and assisted return of the present invention can be utilized, and the rotating cushioning and assisting mechanism of the present invention has reason to be utilized. The exoskeleton joint solution of the present invention is capable of adjusting the joint torsion according to the needs of different body types and has the functions of cushioning and return.

The present invention also discloses an exoskeleton ankle joint cushioning and assisting device, which comprises a connecting rod, a shank connecting rod, a footwear assembly and the rotating cushioning and assisting mechanism; and the shank connecting rod is connected to the inner support heterogeneous member, and the footwear assembly is connected to the rotating outward expanding member through the connecting rod.

By adopting the above technical solution, the present invention has the following technical effects:

The present invention connects the shank connecting rod to the inner support heterogeneous member, and connects the footwear assembly to the rotating outward expanding member; when the foot is plantarflexed and dorsiflexed to drive the inner support heterogeneous member to rotate in the expandable compartment, an outward expanding force is exerted on the first rotating member and the second rotating member to make the two free ends move away from each other, so that the elastic return member is stretched as the free ends of the two rotating members move away from each other; at this time, a work done by the force exerted by the inner support heterogeneous member is converted into elastic potential energy to be stored, which plays a role in cushioning and damping the external force during the storage process; when the external force is over, the elastic potential energy is released and converted into kinetic energy to help the free ends of the two rotating members to move close, thus playing a role in assisted return.

Further, the connecting rod comprises a rod body and a mounting housing, one end of the connecting rod is connected to the mounting housing and the other end is connected to the footwear assembly; and the rotating outward expanding member is located in the mounting housing, and the expansion of the rotating outward expanding member is limited by the wall of the mounting housing. The main function of mounting housing is to prevent the translocation of the rotating outward expanding member, and on the other hand, to set a restriction and limit for the expansion of the rotating outward expanding member, so as to provide limit protection for the plantarflexion and dorsiflexion of the foot.

Further, the exoskeleton ankle joint cushioning and assisting device also includes a rotating shaft and a pivot shaft; the rotating shaft is disposed in the mounting housing, and the inner support heterogeneous member is disposed on the rotating shaft; the first rotating member is provided with a first pivoting hole, the second rotating member is provided with a second pivoting hole, the first pivoting hole and the second pivoting hole are matched and aligned with each other and then mounted on the pivot shaft. The connecting rod is provided for convenience of installation, and the rotating shaft is mounted on the connecting rod, so that the rotation of the inner support heterogeneous member is more stable than that without a rotating shaft, but it doesn't mean that the rotating effect cannot be achieved without a rotating shaft or uniquely determining use of the rotating shaft; the pivot shaft is mounted on the connecting rod for the stable operation of the rotating outward expanding member, and a pivot point will not be displaced, but it does not mean that the pivot shaft must be mounted on the connecting rod, just because it is relatively not stable enough, and it can also be enough to achieve the expansion of the rotating outward expanding member.

Further, the exoskeleton ankle joint cushioning and assisting device also includes a sliding bearing; the inner ring of the sliding bearing is sleeved on the rotating shaft, the inner support heterogeneous member is provided with a mounting opening, and the outer ring of the sliding bearing is fixed into the mounting opening. Sliding bearing is used to reduce unnecessary friction and work waste.

Figure 1:
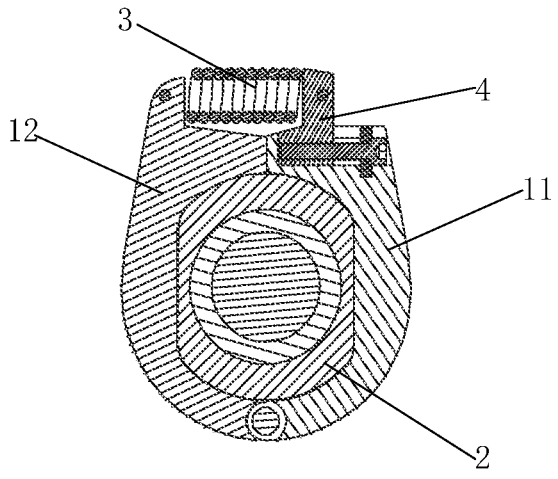
FIG. 1 is a structural schematic diagram of the rotating cushioning and assisting mechanism of the present invention.

In the drawings:
first rotating member 11
second rotating member 12
elastic return member 3
inner support heterogeneous member 2
mounting opening 21
pitch-adjustable member 4
chute 44
limit permanent seat 43
perforation 431
pitch-adjusting slider 41
threaded hole 411
pitch-adjusting threaded member 42
stop portion 421
connecting rod 5
rod body 52
installing housing 51
shank connecting rod 6
shank connecting rod body 61
installing housing base 62
reinforcing rib 621
footwear assembly 7
rotating shaft 14
pivot shaft 13 sliding bearing 15
clamp spring 8

DETAILED DESCRIPTION OF THE EMBODIMENTS

Embodiments of the present invention are described below by way of specific examples, and other advantages and effects of the present invention will be readily apparent to those skilled in the art from the disclosure of this description. The present invention may also be practiced or applied by other different embodiments, and the details of this description may be modified or changed in various ways without departing from the essence of the present invention, based on different views and applications.

Figure 2:
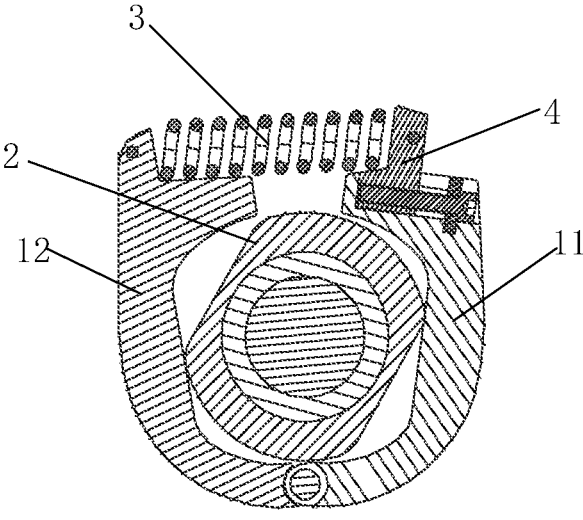
FIG. 2 is a schematic diagram of an outward expansion of the rotating cushioning and assisting mechanism of the present invention.
Figure 3:
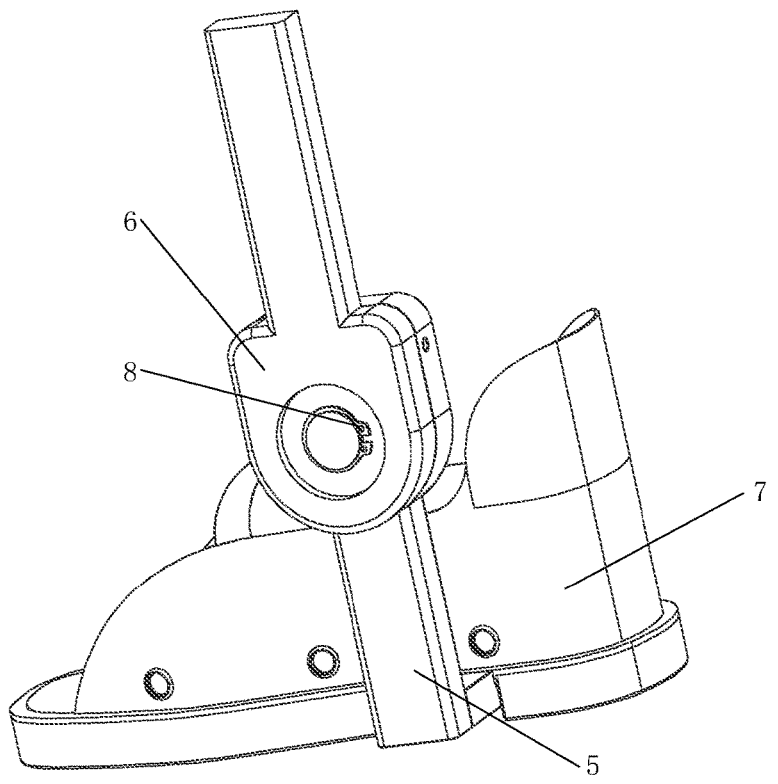
FIG. 3 is a structural schematic diagram of the exoskeleton ankle joint cushioning and assisting device of the present invention.

Referring to FIGS. 1 and 2, the present invention primarily provides an exoskeleton joint mechanism with cushioning and return functions (i.e., resistance cushioning and assisted return), which can adjust the joint torque according to the needs of different body types. The mechanism comprises a rotating outward expanding member, an elastic return member 3 and an inner support heterogeneous member 2; wherein the rotating outward expanding member comprises a first rotating member 11 and a second rotating member 12, which enclose to form an expandable compartment, one ends of the first rotating member 11 and the second rotating member 12 are pivot ends, and the other ends thereof are free ends; the elastic return member 3 is connected to the free ends of the first rotating member 11 and the second rotating member 12; the inner support heterogeneous member 2 is rotationally disposed in the expandable compartment, and with the rotation of the inner support heterogeneous member 2, an outward expanding force is applied to the first rotating member 11 and the second rotating member 12 on both sides of the expandable compartment to stretch the elastic return member 3. The free ends of the first rotating member 11 and the second rotating member 12 are connected through the elastic return member 3, when an external force drives the inner support heterogeneous member 2 to rotate in the expandable compartment, an outward expanding force is exerted on the first rotating member 11 and the second rotating member 12 to make the two free ends move away from each other, so that the elastic return member 3 is stretched as the free ends of the two rotating members move away from each other; at this time, a work done by the force exerted by the inner support heterogeneous member 2 is converted into elastic potential energy to be stored, which plays a role in cushioning and damping the external force during the storage process; when the external force is over, the elastic potential energy is released and converted into kinetic energy to help the free ends of the two rotating members to move close, thus playing a role in assisted return.

Figure 4:
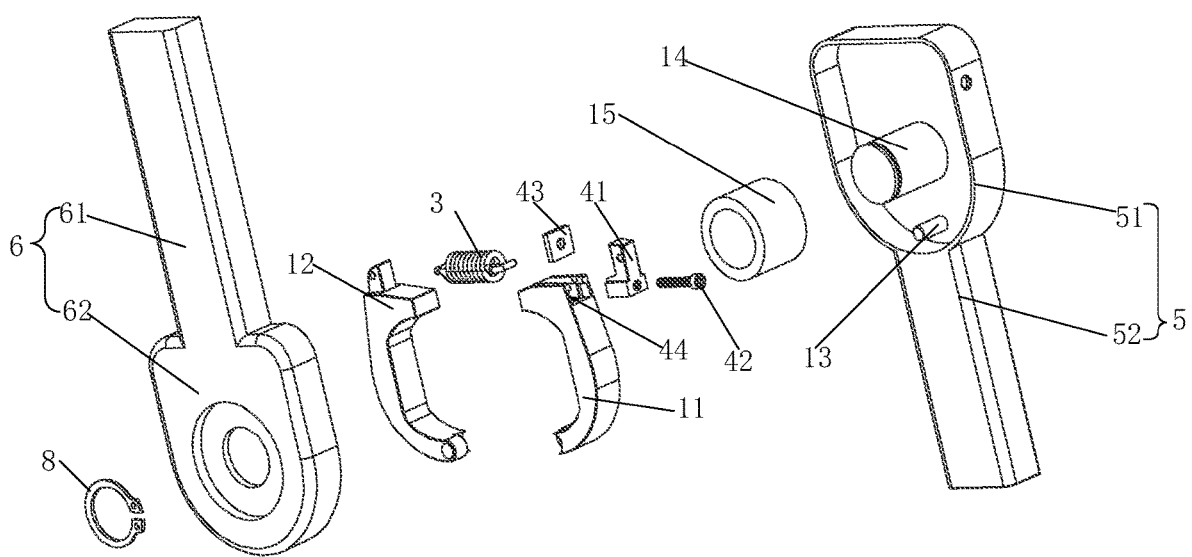
FIG. 4 is an exploded view of the structure of the exoskeleton ankle joint cushioning and assisting device of the present invention.
Figure 5:
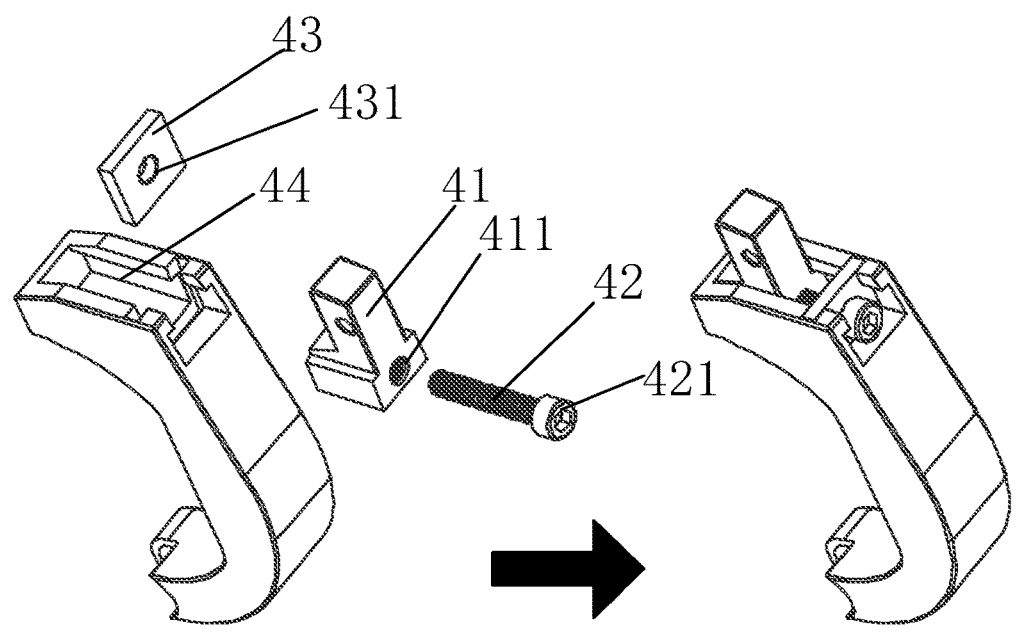
FIG. 5 is an exploded view of the structure of the rotating outward expanding member of the present invention.

The present invention is further described below with reference to the accompanying drawings and specific embodiments:

Referring to FIGS. 4 and 5, in order to provide different damping forces (cushioning forces), it is necessary to adjust the torsion or preloading force of the elastic return member 3 to meet different use requirements. Therefore, the exoskeleton ankle joint cushioning and assisting device also includes a pitch-adjustable member 4, one end of the elastic return member 3 is connected to the first rotating member 11 through the pitch-adjustable member 4, and the other end is connected to the second rotating member 12; the pitch-adjustable member 4 comprises a chute 44, a limit permanent seat 43, a pitch-adjusting slider 41 and a pitch-adjusting threaded member 42; wherein the chute 44 is provided at the free end of the first rotating member 11; the limit permanent seat 43 is disposed on the chute 44 and is limited in the sliding direction of the chute 44, and the limit permanent seat 43 is provided with a perforation 431; the pitch-adjusting slider 41 is slidably disposed in the chute 44 and is provided with a threaded hole 411 facing the perforation 431, and the elastic return member 3 is connected to the pitch-adjusting slider 41; one end of the pitch-adjusting threaded member 42 is threaded through the perforation 431 and screwed into the threaded hole 411, and the other end of the pitch-adjusting threaded member 42 has a stop portion 421 which stops at the limit permanent seat 43. The position of the pitch-adjusting slider 41 in the chute 44 is driven by a thread depth of the pitch-adjusting threaded member 42 in the pitch-adjusting slider 41, which realizes the pre-stretching of the elastic return member 3. It is well known that the elastic force brought by elasticity increases proportionally with the stretching of the elastic member, so it plays a role in adjusting the torque to adapt to different users.

As a preferred implementation of the present embodiment, the limit permanent seat 43 can also be disposed on the free end of the first rotating member 11. It is not specifically illustrated in this embodiment, but it should be known to those skilled in the art that the limit permanent seat 43 serves as a member for providing a pitch adjustment fulcrum in cooperation with the stop portion 421 of the pitch-adjusting threaded member 42, and its core function is to maintain the position unchanged. It is a practical choice to dispose the limit permanent seat at the chute 44 or the free end of the first rotating member 11.

As a preferred implementation of the present embodiment, the elastic return member 3 includes, but is not limited to, a spring or an elastic rubber resin. Other members that can achieve elastic stretching and return can also be adopted in theory.

In the above provided solutions, when an outer member is connected to the inner support heterogeneous member 2 for rotation, it is sufficient to complete the damping cushion of force and the assistance of return.

However, although the solution described above alone can achieve the desired effect, it is not stable enough to play a role in limit protection. Thus, the present invention also includes a connecting rod 5, which comprises a rod body 52 and a mounting housing 51, one end of the rod body 52 is connected to the mounting housing 51 and the other end is connected to an external structure; and the rotating outward expanding member is located in the mounting housing 51, and the expansion of the rotating outward expanding member is limited by the wall of the mounting housing 51. The main function of the mounting housing 51 is to prevent translocation of the rotating outward expanding member by cooperating with the following pivot shaft 13, and on the other hand, to set a restriction and limit for the expansion of the rotating outward expanding member, that is, the expansion is limited to a certain extent.

As a preferred implementation of the present embodiment, the exoskeleton ankle joint cushioning and assisting device also includes a rotating shaft 14 and a pivot shaft 13; the rotating shaft 14 is disposed in the mounting housing 51, and the inner support heterogeneous member 2 is disposed on the rotating shaft 14; the first rotating member 11 is provided with a first pivoting hole, the second rotating member 12 is provided with a second pivoting hole, the first pivoting hole and the second pivoting hole are matched and aligned with each other and then mounted on the pivot shaft 13. The connecting rod 5 is provided for convenience of installation, and the rotating shaft 14 is mounted on the connecting rod 5, so that the rotation of the inner support heterogeneous member 2 is more stable than that without the rotating shaft 14, but it doesn't mean that the rotating effect cannot be achieved without the rotating shaft 14 or uniquely determining use of the rotating shaft 14; the pivot shaft 13 is mounted on the connecting rod 5 for the stable operation of the rotating outward expanding member, and a pivot point will not be displaced.

As a preferred implementation of the present embodiment, the exoskeleton ankle joint cushioning and assisting device also includes a sliding bearing 15, the inner ring of the sliding bearing 15 is sleeved on the rotating shaft 14, the inner support heterogeneous member 2 is provided with a mounting opening 21, and the outer ring of the sliding bearing 15 is fixed into the mounting opening 21. Sliding bearing 15 is used to reduce unnecessary friction and work waste.

As a preferred implementation of the present embodiment, the shape of the expandable compartment matches the shape of the inner support heterogeneous member 2. The inner support heterogeneous member 2 is a rectangular block, and two opposite surfaces of the rectangular block are disposed as arc-shaped surfaces.

The present invention also discloses an application of the rotating cushioning and assisting mechanism for cushioning and assisting in the exoskeleton joint rehabilitation exercise. Specifically, as long as the multi-degree of freedom movement of joints is involved, the principle of damping force cushioning and assisted return of the present invention can be utilized, and the rotating cushioning and assisting mechanism of the present invention has reason to be utilized. The exoskeleton joint solution of the present invention is capable of adjusting the joint torsion according to the needs of different body types and has the functions of cushioning and return.

Application embodiments:
1. The application of the rotating cushioning and assisting mechanism in the exoskeleton shoulder joint rehabilitation exercise for cushioning and assisting can facilitate the rehabilitation training on the swing of the arm. Specifically, the mechanism is adaptively tied to the shoulder, and the arm can be linked with the inner support heterogeneous member 2. This embodiment is not specifically illustrated, but those skilled in the art can undoubtedly conclude it.
2. The application of the rotating cushioning and assisting mechanism in the exoskeleton ankle joint rehabilitation exercise for cushioning and assisting can perform plantarflexion/dorsiflexion of the foot for foot ankle joint rehabilitation training. Specifically, the mechanism is adaptively disposed in the ankle joint, and the effect embodiment is presented together with the following technical solutions.

Referring to FIGS. 1, 2, 3 and 4, the present invention also discloses an exoskeleton ankle joint cushioning and assisting device, which comprises a shank connecting rod 6, a footwear assembly 7 and the rotating cushioning and assisting mechanism as described above; the shank connecting rod 6 is connected to the inner support heterogeneous member 2, and the footwear assembly 7 is connected to the rotating outward expanding member. The present invention connects the shank connecting rod 6 to the inner support heterogeneous member 2, and connects the footwear assembly 7 to the rotating outward expanding member, when the foot is plantarflexed and dorsiflexed to drive the inner support heterogeneous member 2 to rotate in the expandable compartment, an outward expanding force is exerted on the first rotating member 11 and the second rotating member 12 to make the two free ends move away from each other, so that the elastic return member 3 is stretched as the free ends of the two rotating members move away from each other; at this time, a work done by the force exerted by the inner support heterogeneous member 2 is converted into elastic potential energy to be stored, which plays a role in cushioning and damping the external force during the storage process; when the external force is over, the elastic potential energy is released and converted into kinetic energy to help the free ends of the two rotating members to move close, thus playing a role in assisted return.

The present invention is further described below with reference to the accompanying drawings and specific embodiments:

In order to enable the rotating cushioning and assisting mechanism to be adaptively disposed in the ankle joint, as a preferred implementation of the present embodiment, the exoskeleton ankle joint cushioning and assisting device also includes a connecting rod 5, which comprises a rod body 52 and a mounting housing 51, one end of the connecting rod 5 is connected to the mounting housing 51, the other end is connected to the footwear assembly 7, and the shank connecting rod 6 is connected to the inner support heterogeneous member 2. A relative rotation of the foot and the shank is acted on the inner support heterogeneous member 2 and the rotating outward expanding member.

Further, the rotating outward expanding member is located in the mounting housing 51, and the expansion of the rotating outward expanding member is limited by the wall of the mounting housing 51. The main function of mounting housing 51 is to prevent the translocation of the rotating outward expanding member, and on the other hand, to set a restriction and limit for the expansion of the rotating outward expanding member, so as to provide limit protection for the plantarflexion and dorsiflexion of the foot.

As a preferred implementation of the present embodiment, the exoskeleton ankle joint cushioning and assisting device also includes a rotating shaft 14 and a pivot shaft 13, the rotating shaft 14 is disposed in the mounting housing 51, and the inner support heterogeneous member 2 is disposed on the rotating shaft 14; the first rotating member 11 is provided with a first pivoting hole, the second rotating member 12 is provided with a second pivoting hole, the first pivoting hole and the second pivoting hole are matched and aligned with each other and then mounted on the pivot shaft 13. The connecting rod 5 is provided for convenience of installation, and the rotating shaft 14 is mounted on the connecting rod 5, so that the rotation of the inner support heterogeneous member 2 is more stable than that without the rotating shaft 14, but it doesn't mean that the rotating effect cannot be achieved without the rotating shaft 14 or uniquely determining use of the rotating shaft 14; the pivot shaft 13 is mounted on the connecting rod 5 for the stable operation of the rotating outward expanding member, and a pivot point will not be displaced, but it does not mean that the pivot shaft 13 must be mounted on the connecting rod 5, but it is relatively not stable enough, and it can also be enough to achieve the expansion of the rotating outward expanding member.

As a preferred implementation of the present embodiment, the exoskeleton ankle joint cushioning and assisting device also includes a sliding bearing 15, the inner ring of the sliding bearing 15 is sleeved on the rotating shaft 14, the inner support heterogeneous member 2 is provided with a mounting opening 21, and the outer ring of the sliding bearing 15 is fixed into the mounting opening 21. Sliding bearing 15 is used to reduce unnecessary friction and work waste.

Figure 6:
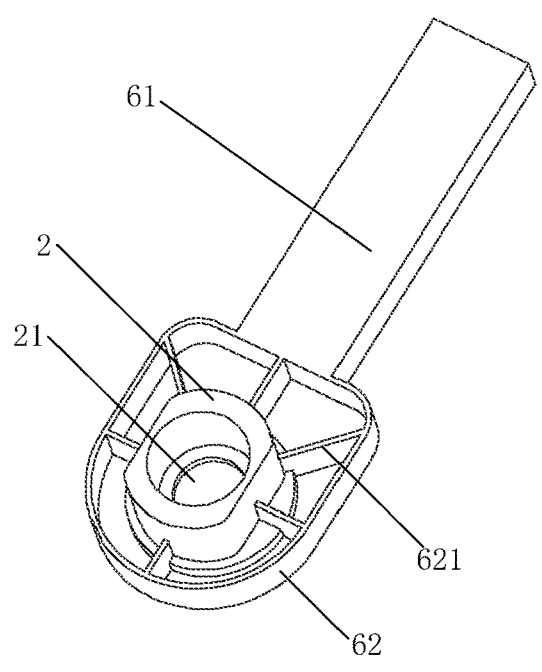
FIG. 6 is a structural schematic diagram of a shank assembly in the exoskeleton ankle joint cushioning and assisting device of the present invention.

Referring to FIGS. 4 and 6, as a preferred implementation of the present embodiment, the shank connecting rod 6 comprises a shank connecting rod body 61 and a mounting housing base 62 connected to the shank connecting rod body 61. The inner support heterogeneous member 2 is disposed in the mounting housing base 62, and a reinforcing rib 621 is disposed between the outer wall of the inner support heterogeneous member 2 and the inner wall of the mounting housing base 62. The mounting opening 21 of the inner support heterogeneous member 2 is fixed by a clamp spring 8 after being mounted to the rotating shaft 14.

As a preferred implementation of the present embodiment, the shape of the expandable compartment matches the shape of the inner support heterogeneous member 2, forming an "0" shaped heterostructure with the mounting opening 21 in the inner support heterogeneous member 2. The inner support heterogeneous member 2 is a rectangular block, and two opposite surfaces of the rectangular block are disposed as arc-shaped surfaces.

Figure 7:
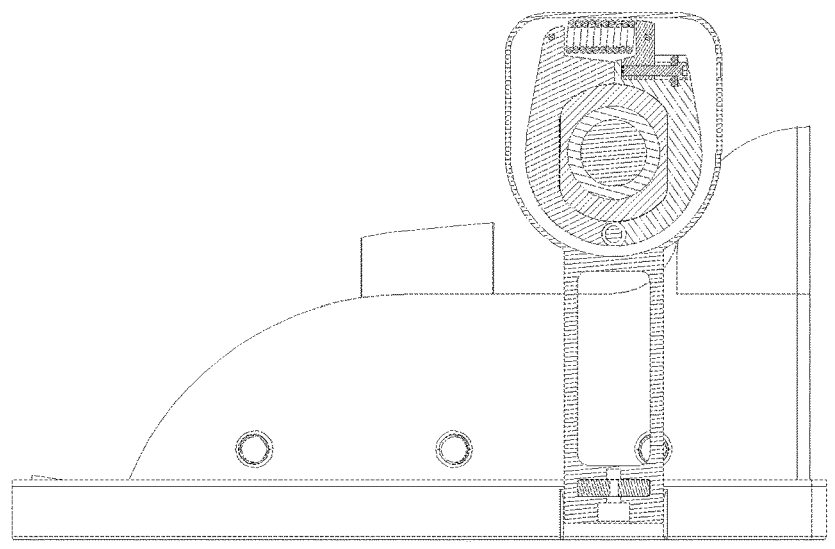
FIG. 7 is an initial state diagram of the exoskeleton ankle joint cushioning and assisting device of the present invention.
Figure 8:
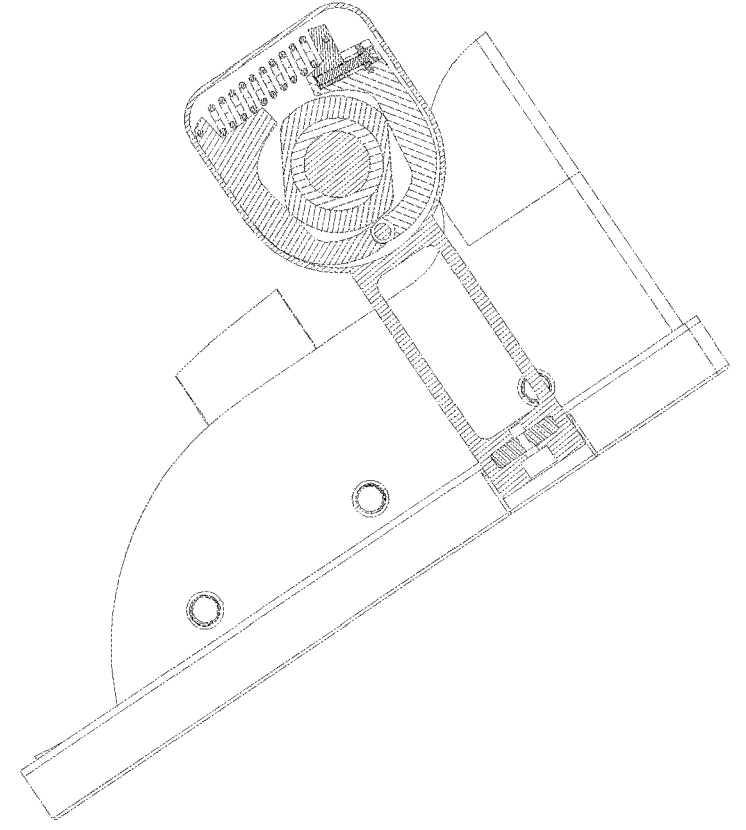
FIG. 8 is a plantarflexion state diagram of the exoskeleton ankle joint cushioning and assisting device of the present invention.
Figure 9:
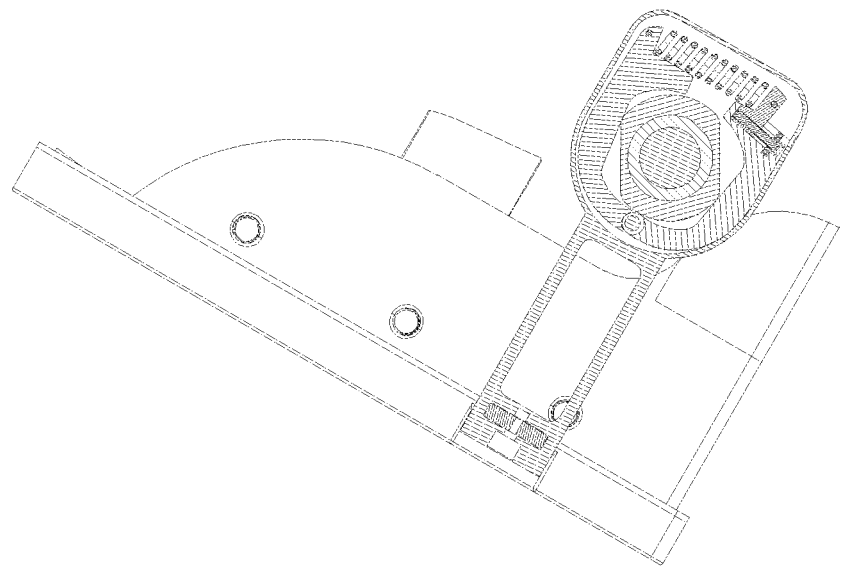
FIG. 9 is a dorsiflexion state diagram of the exoskeleton ankle joint cushioning and assisting device of the present invention.

Referring to FIGS. 7, 8 and 9, the principle of this embodiment acting on the ankle joint is as follows:

In an initial state, the shank connecting rod 6 and the connecting rod 5 form an included angle of 180°, and the first rotating member 11 and the second rotating member 12 engage the inner support heterostructure 2 of the shank connecting rod 6 with the pivot shaft 14 as a fulcrum under the action of the elastic return member 3.

When the foot makes plantarflexion movement, the inner support heterogeneous member 2 on the shank connecting rod 6 supports and opens the first rotating member 11 and the second rotating member 12, the elastic return member 3 is driven to stretch to store elastic potential energy. When the outer side of the rotating outward expanding member is in contact with the inner wall of the mounting housing 51, a plantarflexion angle is limited, and at this time, the elastic potential energy is released by rotation to realize assisted return.

When the foot makes dorsiflexion movement, its principle is the same as plantarflexion movement, so it will not be repeated here.

When the user needs to adjust the ankle cushioning due to great difference in body shape or other reasons, the pitch-adjusting thread 42 can be adjusted in the initial state to drive the pitch-adjusting slider 41 to slide, change the pre-loading force of the elastic return member 3, change the torque value at the ankle joint, and realize the cushioning adjustment.

It should be noted that the structure, scale, size, etc. shown in the drawings of this description, are only used to cooperate with the contents disclosed in the description, for people skilled in the art to understand and read, it is not intended to limit the conditions under which the present invention can be implemented, so it has no technical significance. Any modification of structure, change of proportional relationship or adjustment of size should still fall within the scope of the technical content disclosed by the present invention without affecting the effect and purpose achieved by the present invention. Meanwhile, the terms such as "upper", "lower", "left", "right", "middle" and "one" used in this description are for ease of description only, and are not intended to limit the practicable scope of the present invention. Changes or adjustments in their relative relations are also regarded as practicable scope of the present invention without substantial changes in technical contents.

Various changes may be made to the present invention by those of ordinary skilled in the art based on the above description. Thus, certain details in the embodiments are not intended to limit the present invention without violating the essence of the claims of the present invention, and the present invention is to be protected within the scope defined in the appended claims.

What is claimed is:

1. A rotating cushioning and assisting mechanism, comprising:
   a rotating outward expanding member comprising a first rotating member and a second rotating member, which enclose to form an expandable compartment, one end of the first rotating member and the second rotating member are pivot ends, and the other ends of the first rotating member and the second rotating member are free ends;
   an elastic return member connected to the free ends of the first rotating member and the second rotating member; and
   an inner support heterogeneous member rotationally disposed in the expandable compartment, and
   an outward expanding force is applied on the first rotating member and the second rotating member on both sides of the expandable compartment along with the rotation of the inner support heterogeneous member, to stretch the elastic return member;
   a pitch-adjustable member, one end of the elastic return member is connected to the first rotating member through the pitch-adjustable member, and the other end is connected to the second rotating member; and the pitch-adjustable member comprises:
   a chute provided at the free end of the first rotating member;
   a limit permanent seat disposed in the chute and limited in the sliding direction of the chute, and provided with a perforation;
   a pitch-adjusting slider disposed in the chute and provided with a threaded hole facing the perforation, and the elastic return member being connected to the pitch-adjusting slider; and a pitch-adjusting threaded member,
   one end of which threaded through the perforation and screwed into the threaded hole, and the other end having a stop portion that stops at the limit permanent seat.

2. The rotating cushioning and assisting mechanism of claim 1, characterized in: the limit permanent seat is disposed on the free end of the first rotating member.

3. The rotating cushioning and assisting mechanism of claim 1, characterized in: the elastic return member is a spring or an elastic rubber resin.

4. The rotating cushioning and assisting mechanism of claim 1, comprising a connecting rod comprising a rod body and a mounting housing, one end of the rod body is connected to the mounting housing and the other end is connected to an external structure; and the rotating outward expanding member is located in the mounting housing, and the expansion of the rotating outward expanding member is limited by the wall of the mounting housing.

5. An application of the rotating cushioning and assisting mechanism of claim 1 in an exoskeleton joint rehabilitation exercise device.

6. An exoskeleton ankle joint cushioning and assisting device, comprising a connecting rod, a shank connecting rod, a footwear assembly and the rotating cushioning and assisting mechanism of claim 1; and the shank connecting rod is connected to the inner support heterogeneous member, and the footwear assembly is connected to the rotating outward expanding member through the connecting rod.

7. The cushioning and assisting device of claim 6, the connecting rod comprises a rod body and a mounting housing, one end of the connecting rod is connected to the mounting housing and the other end is connected to the footwear assembly;
   and the rotating outward expanding member is located in the mounting housing, and the expansion of the rotating outward expanding member is limited by the wall of the mounting housing.

8. The cushioning and assisting device of claim 7, comprising a rotating shaft and a pivot shaft; the rotating shaft is disposed in the mounting housing, and the inner support heterogeneous member is disposed on the rotating shaft; and the first rotating member is provided with a first pivoting hole, the second rotating member is provided with a second pivoting hole, and the first pivoting hole and the second pivoting hole are matched and aligned with each other and then mounted on the pivot shaft.

9. The cushioning and assisting device of claim 8, comprising a sliding bearing, the inner ring of the sliding bearing is sleeved on the rotating shaft, the inner support heterogeneous member is provided with a mounting opening, and the outer ring of the sliding bearing is fixed into the mounting opening.

10. The rotating cushioning and assisting mechanism of claim 1, characterized in:
    the elastic return member is a spring or an elastic rubber resin.

11. The rotating cushioning and assisting mechanism of claim 1, characterized in:
    the elastic return member is a spring or an elastic rubber resin.

12. An application of the rotating cushioning and assisting mechanism of claim 2 in an exoskeleton joint rehabilitation exercise device.

13. An application of the rotating cushioning and assisting mechanism of claim 2 in an exoskeleton joint rehabilitation exercise device.

14. An application of the rotating cushioning and assisting mechanism of claim 3 in an exoskeleton joint rehabilitation exercise device.

15. An application of the rotating cushioning and assisting mechanism of claim 4 in an exoskeleton joint rehabilitation exercise device.

16. An application of the rotating cushioning and assisting mechanism of claim 10 in an exoskeleton joint rehabilitation exercise device.

17. An application of the rotating cushioning and assisting mechanism of claim 11 in an exoskeleton joint rehabilitation exercise device.

18. An exoskeleton ankle joint cushioning and assisting device, comprising a connecting rod, a shank connecting rod, a footwear assembly and the rotating cushioning and assisting mechanism of claim 1; and the shank connecting rod is connected to the inner support heterogeneous member, and the footwear assembly is connected to the rotating outward expanding member through the connecting rod.

19. An exoskeleton ankle joint cushioning and assisting device, comprising a connecting rod, a shank connecting rod, a footwear assembly and the rotating cushioning and assisting mechanism of claim 2; and the shank connecting rod is connected to the inner support heterogeneous member, and the footwear assembly is connected to the rotating outward expanding member through the connecting rod.

\* \* \* \* \*